United States Patent
Lee et al.

(10) Patent No.: US 11,186,633 B2
(45) Date of Patent: Nov. 30, 2021

(54) SPECIFIC MONOCLONAL ANTIBODY TO ACETYLATED MOUSE BUBR1 AND PREPARATION METHOD THEREFOR

(71) Applicant: Seoul National University R&DB Foundation, Seoul (KR)

(72) Inventors: Hyunsook Lee, Seoul (KR); Mi-Sun Kwon, Seoul (KR); Inai Park, Seoul (KR); Hyeon-Jong Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 656 days.

(21) Appl. No.: 16/070,828

(22) PCT Filed: Jan. 20, 2017

(86) PCT No.: PCT/KR2017/000746
§ 371 (c)(1),
(2) Date: Mar. 20, 2019

(87) PCT Pub. No.: WO2017/126944
PCT Pub. Date: Jul. 27, 2017

(65) Prior Publication Data
US 2019/0202910 A1 Jul. 4, 2019

(30) Foreign Application Priority Data

Jan. 20, 2016 (KR) ........................ 10-2016-0006851
Jan. 20, 2017 (KR) ........................ 10-2017-0009988

(51) Int. Cl.
*C07K 16/28* (2006.01)
*G01N 33/68* (2006.01)
*C07K 16/18* (2006.01)
*G01N 33/539* (2006.01)

(52) U.S. Cl.
CPC .............. *C07K 16/28* (2013.01); *C07K 16/18* (2013.01); *G01N 33/539* (2013.01); *G01N 33/68* (2013.01); *C07K 2317/34* (2013.01)

(58) Field of Classification Search
CPC .... C07K 16/28; C07K 16/18; C07K 2317/34; G01N 33/539; G01N 33/68; C12Q 1/48
See application file for complete search history.

(56) References Cited

U.S. PATENT DOCUMENTS

2008/0102477 A1   5/2008  Lee et al.

FOREIGN PATENT DOCUMENTS

KR   10-2011-0019495   2/2011

OTHER PUBLICATIONS

Lee, "How Chromosome Mis-Segregation Leads to Cancer: Lessons from BubR1 Mouse Models", Molecules and Cells, Sep. 26, 2014 (Online), vol. 37, No. 10, pp. 713-718.

Park et al., "Loss of BubR1 acetylation Causes Defects in Spindle Assembly Checkpoint Signaling and Promotes Tumor Formation", The Journal of Cell Biology, Jul. 22, 2013, vol. 202, No. 2, pp. 295-309.

Choi et al.. "BubR1 acetylation at Prometaphase is Required for Modulating APC/C Activity and Timing of Mitosis", The EMBO journal, 2009, vol. 28, No. 14, pp. 2077-2089.

S. S. Taylor et al., "The spindle checkpoint: a quality control mechanism which ensures accurate chromosome segregation", Chromosome Research, vol. 12, pp. 599-616, 2004.

H. Yu, "Regulation of APC-Cdc20 by the spindle checkpoint", Current Opinion in Cell Biology, vol. 14, pp. 706-714, 2002.

G. J. P. L. Kops et al., "On the road to cancer: Aneuploidy and the mitotic checkpoint", Nature Reviews Cancer, vol. 5, pp. 773-785, 2005.

G. A. Pihan et al., "The mitotic machinery as a source of genetic instability in cancer", Cancer Biology, vol. 9, pp. 289-302, 1999.

D. Hanahan et al., "The Hallmarks of Cancer", Cell, vol. 100, pp. 57-70, 2000.

R. Li et al., Aneuploidy vs. gene mutation hypothesis of cancer: Recent study claims mutation but is found to support aneuploidy, PNAS, vol. 97, No. 7, pp. 3236-3241, 2000.

S. Rossi et al., A Comparative Study Between a Novel Category of Immunoreagents and the Corresponding Mouse Monoclonal Antibodies, Anatomic Pathology, Rabbit Monoclonal Antibodies, vol. 124, No. 2, pp. 295-302, 2005.

R. Rocha et al., "Rabbit monoclonal antibodies show higher sensitivity than mouse monoclonals for estrogen and progesterone receptor evaluation in breast cancer by immunohistochemistry", Pathology Research and Practice, vol. 204, No. 9, pp. 655-662, 2008.

Guo-Zhong Tao et al., "Bispecific and human disease-related anti-keratin rabbit monoclonal antibodies", Experimental Cell Research, vol. 312, pp. 411-422, 2006.

T. J. G. Raybould et al., "Production of Stable Rabbit-Mouse Hybridomas That Secrete Rabbit mAb of Defined Specificity" Science, vol. 240, pp. 1788-1790, 1988.

L. Feng et al., "Rabbit monoclonal antibody: potential application in cancer therapy", American Journal of Translational Research, vol. 3, No. 3, pp. 269-274, 2011.

H. Spieker-Polet et al., "Rabbit monoclonal antibodies: Generating a fusion partner to produce rabbit-rabbit hybridomas", Proceedings of the National Academy of Sciences of the United States of America, vol. 92, No. 20, pp. 9348-9352, 1995.

Pi-Chen Yam et al., "Generation of rabbit monoclonal antibodies", Chapter 5, Methods in Molecular Biology, vol. 1131, pp. 71-79, 2014, Human Press, Methods and Protocols, Second Edition, Springer Protocols.

*Primary Examiner* — Alana Harris Dent
(74) *Attorney, Agent, or Firm* — Lex IP Meister, PLLC

(57) ABSTRACT

Provided is a rabbit monoclonal antibody to acetylated mouse BubR1 and a preparation method therefor and, more particularly, provides the use of the monoclonal antibody in a method for measuring the activity of cell division checkpoints on the basis of a degree of acetylation of BubR1, a method for detecting a tumor disease on the basis of aberrant cell division, a method for diagnosing cancer, a method for screening anti-cancer agents, or a method for regulating a cell division cycle.

8 Claims, 3 Drawing Sheets
Specification includes a Sequence Listing.

[FIG. 1]
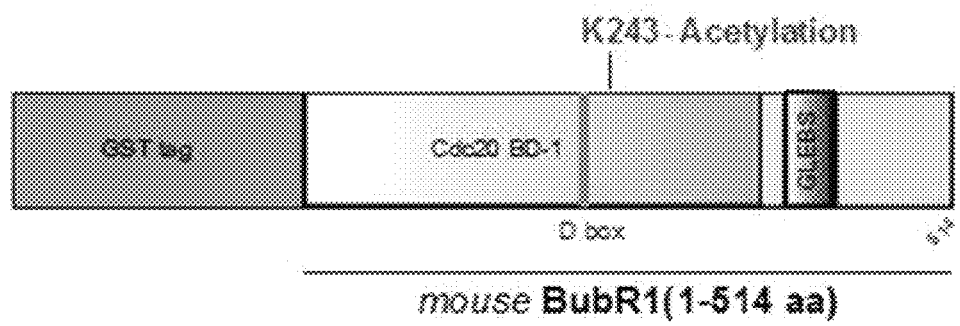
[FIG. 2]
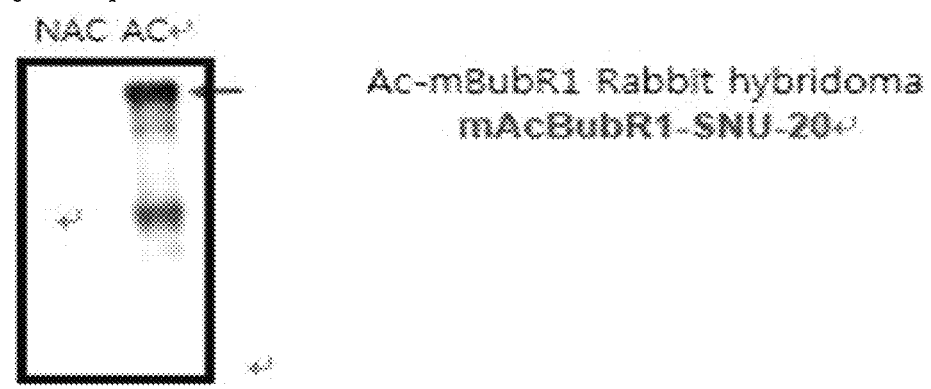
[FIG. 3]
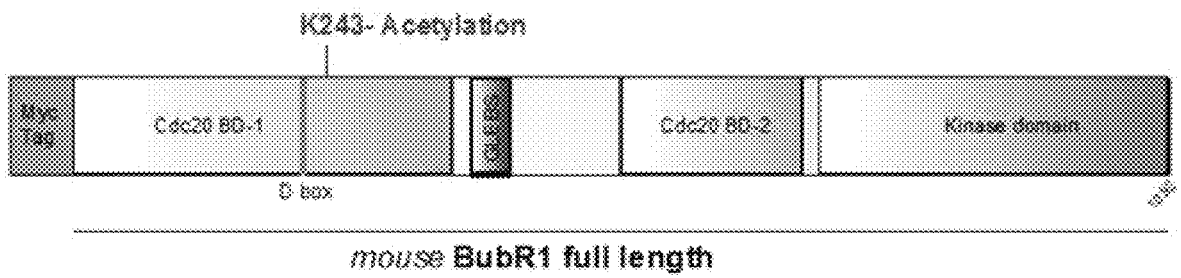

[FIG. 4]
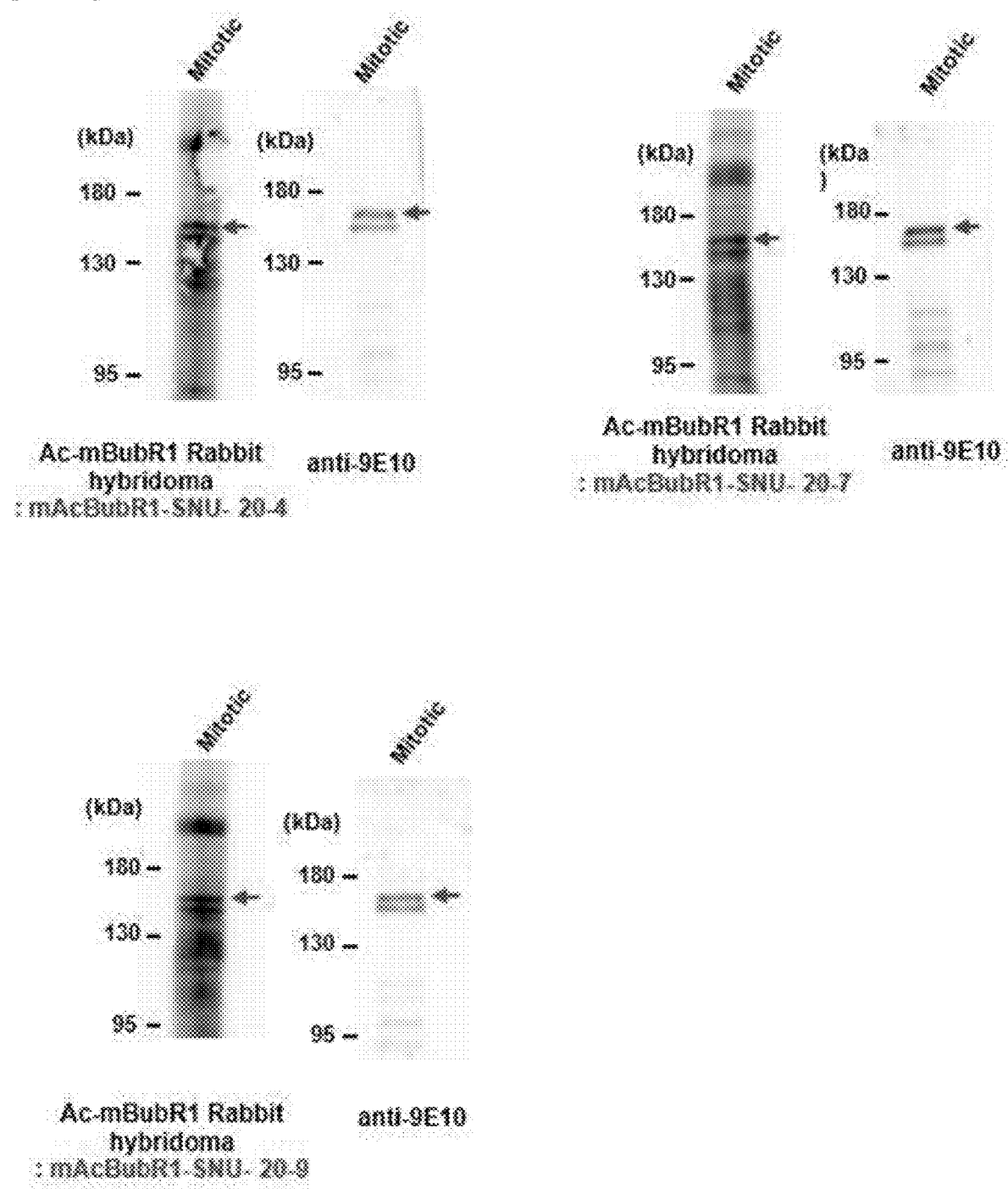

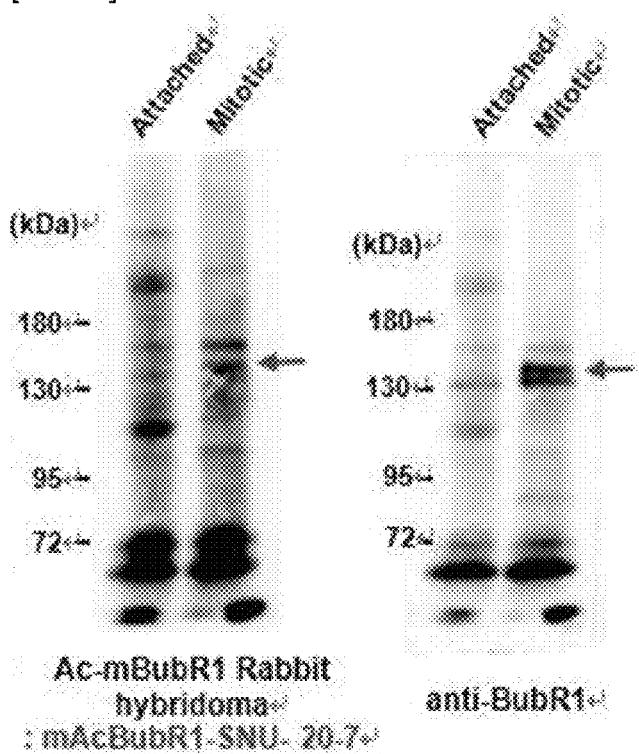

SPECIFIC MONOCLONAL ANTIBODY TO ACETYLATED MOUSE BUBR1 AND PREPARATION METHOD THEREFOR

TECHNICAL FIELD

The present invention relates to a rabbit-immune and specific monoclonal antibody against acetylated mouse BubR1 and a method of preparing the same. More particularly, the present invention provides the specific monoclonal antibody, a hybridoma producing the specific monoclonal antibody, and a method of measuring cell division checkpoint activity based on acetylation degree of mouse BubR1, detecting a disease associated with abnormal cell division, diagnosing a cancer, and screening an anticancer agent, or regulating cell division cycle, using the antibody.

BACKGROUND ART

The most important factor in cell division is to accurately convey the same genetic information of a mother cell to a daughter cell. In particular, the chromosome segregation stage when genetic information is replicated and transferred to daughter cells, that is, the transition period from metaphase to anaphase of cell division, is the peak of cell division, and the transfer of the complete genome to daughter cells requires normal operation of a spindle assembly checkpoint (SAC) [Taylor S S, Scott M I, Holland A J (2004) The spindle checkpoint: a quality control mechanism which ensures accurate chromosome segregation. Chromosome Res 12: 599-616]. Normally, cell division is usually terminated within 30 minutes, but if even one chromosome does not properly adhere to spindle, cell division will be delayed for up to 16 hours. The SAC functions to regulate the cell cycle, wherein activated SAC inhibits anaphase promoting complex (APC/C) which is required for anaphase process [Yu H (2002) Regulation of APC-Cdc20 by the spindle checkpoint. Curr Opin Cell Biol 14: 706-714]. APC/C is E3 ligase forming a multimeric complex, which destroys securin and cyclin B [Yu, ibid]. If the SAC fails to function properly, the cell will die, or become aneuploid, which is known to be an important feature of cancer cells [Kops G J, Weaver B A, Cleveland D W (2005) On the road to cancer: aneuploidy and the mitotic checkpoint. Nat Rev Cancer 5: 773-785; Pihan G. A. et al (1999) Cancer Biology 9: 289-302]. In addition, a failure of SAC can lead to a chromosomal instability (CIN) cancer that is progressive and difficult to treat [Hannahan D et al, Cell 100: 57-70 (2000); Li R et al. PNAS 97: 3236-3241 (2000)]. Since cancer cells divide unlimitedly, controlling cell division is a shortcut to cancer therapy. For this, it is necessary to examine the interactions of several factors at cell division checkpoints and the mechanism of their regulation, and to develop substances that can check the activity of these checkpoints. Out of the factors that constitute the cell division checkpoint SAC, BubR1 is known to be important for inhibiting APC/C by directly binding to APC/C [Yu, ibid]. However, the APC/C regulatory mechanism of this BubR1 protein and antibodies specifically recognizing this protein are unknown.

Furthermore, up to present, any antibodies capable of detecting mouse acetyl BubR1 protein have not been known. A mouse model is representative as an animal capable of being used for in vivo experiment, but it is impossible to carry out an experiment such as drug screening to find novel anticancer agents using a conventional antibody in mouse model. Therefore, development of an antibody capable of recognizing the mouse acetyl BubR1 protein is required.

In addition, a monoclonal antibody is an antibody recognizing one epitope, and thus, the monoclonal antibody has low cross-reactivity and can be produced semi-permanently for the purpose of identifying the presence of the epitope. Therefore, the monoclonal antibody has merit in stable supply. In addition, since it has high specificity and high affinity, it is widely used not only for the purpose of detecting a specific protein but also as a therapeutic antibody (antibody medicine) and diagnostic tool for cancer. A rabbit immune monoclonal antibody has been used as an ideal monoclonal antibody for research and diagnosis. In particular, a rabbit immune antibody has been reported to have higher affinity and higher specificity than other antibodies [Rossi, S et al., Am J Clin Pathol., 124 (2), 295-302 (2005); Rocha R et al., Pathol Res Pract, 204 (9), 655-662 (2008); Tao, G. Z. et al, Exp Cell Res 312, 411-422 (2006)]. In particular, rabbits are known to produce antibodies against antigens with greater immunogenicity than mice and other animals [Raybould, T J et al, Science 240, 1788-1790 (1988): Feng, L et al, Am J Transl Res 3, 269-274 (2011)].

The present inventors have revealed that BubR1 acetylation acts as a molecular switch to control cell division checkpoint activity, suggesting that BubR1 acetylation can be used as a cell division checkpoint specific indicator [Choi et al., *EMBO Journal*, 28 (14), 2077-2089 (2009)]. BubR1$^{K243R/+}$ mice embryonic fibroblasts (MEFs) having inactivated BubR1 acetylation site has been found to develop spontaneous tumors at around 40% ratio. BubR1 acetylation has been shown to regulate the two most important cell division events in mitotic phase, kinetochore-spindle binding and maintenance of spindle assembly checkpoint [Park et al., *J. Cell Biol.*, 202 (2), 295-309 (2013)].

Korean Patent Publication No. 10-2011-0019495 discloses a method for producing a polyclonal antibody against BubR1 derived from human, *Mus musculus, Galus gallus, Xenopus laevis*. However, the method of producing a rabbit immune monoclonal antibody against acetylated mouse BubR1 has not been disclosed or suggested in any references.

DISCLOSURE

Technical Problem

Therefore, an object of the present invention is to provide a novel hybridoma cell line for rabbit-immunized acetylated mouse BubR1, a rabbit immune monoclonal antibody derived from the cell line, and a method of producing the same.

Another object of the present invention is to provide a use of the monoclonal antibody.

Still another object of the present invention is to provide a kit for diagnosing a cancer.

Other object of the present invention can be found within the scope of the examples illustrated in the detailed description.

Technical Solution

The above object of the present invention can be achieved by steps of: determining a target peptide antigen for an acetylated mouse BubR1 and producing polyclonal hybridoma cells;

selecting a BubR1-specific polyclonal hybridoma mAcBubR1-SNU-20 (Korean Cell Line Bank; KCLRF-BP- 00390, deposited on 2017 Jan. 19) cells from the polyclonal hybridoma cells produced in the above step using GST-tagged mouse BubR1 (amino acids 1-514) recombinant protein;

selecting monoclonal hybridoma cells from the BubR1-specific polyclonal hybridoma mAcBubR1-SNU-20 cells, culturing the selected monoclonal hybridoma cells, and purifying the culture solution;

conducting immunoprecipitation using HeLa cells and western blotting for selecting monoclonal antibodies that are specific to acetylated mouse BubR1 from the culture solution purified in the above step, to obtain monoclonal antibodies against acetylated mouse BubR1 from culture solution of monoclonal hybridoma cells mAcBubR1-SNU-20-4 (Korean Cell Line Bank, KCLRF-BP-00391, deposited on 2017 Jan. 19), mAcBubR1-SNU-20-7(Korean Cell Line Bank, KCLRF-BP-00392, deposited on 2017 Jan. 19), and mAcBubR1-SNU-20-9(Korean Cell Line Bank, KCLRF-BP-00393, deposited on 2017 Jan. 19); and conducting immunoprecipitation using mouse embryonic fibroblasts and western blotting for selecting monoclonal antibodies that are specific to endogenous acetylated mouse BubR1 from the obtained monoclonal antibodies, to obtain a novel monoclonal antibody mAcBubR1-SNU-20-7 having rabbit immune specificity.

Effect of the Invention

The present invention provides a rabbit monoclonal antibody against rabbit-immunized acetylated mouse BubR1 which is superior in specificity and reactivity to a mouse monoclonal antibody and a method for producing the same. In addition, the rabbit monoclonal antibody has excellent effects in measuring cell division checkpoint activity using acetylation degree of BubR1 as a scale, detecting a disease associated with abnormal cell division, diagnosing a cancer, and screening an anticancer agent, or regulating cell division cycle.

BRIEF DESCRIPTION OF DRAWINGS

FIG. 1 is a schematic diagram of a novel GST-tagged mouse BubR1 (amino acids 1-514) recombinant protein according to the present invention.

FIG. 2 is a western blotting image showing that a culture solution of the anti-mouse acetylated BubR1 polyclonal hybridomas according to the present invention specifically recognize acetylated BubR1 at 243 lysine residue.

FIG. 3 is a schematic diagram of Myc-tagged mouse BubR1 according to the present invention.

FIG. 4 is a photograph of western blotting results obtained after transfecting HeLa cells with a plasmid containing Myc-tagged mouse BubR1, and then, performing immunoprecipitation of monoclonal antibodies mAcBubR1-SNU-20-4, mAcBubR1-SNU-20-7, and mAcBubR1-SNU-20-9, that specifically bind to mouse acetylated BubR1.

FIG. 5 is a photograph of western blotting results obtained after performing immunoprecipitation of monoclonal antibody mAcBubR1-SNU-20-7 that specifically binds to mouse acetylated BubR1 using mouse embryonic fibroblasts.

DETAILED DESCRIPTION OF THE EMBODIMENTS

The present invention discloses monoclonal antibodies against acetylated mouse BubR1 and preparation methods thereof.

Hereinafter, the present invention will be described in more detail with reference to examples. However, the following examples are intended to illustrate the invention and are not intended to limit the scope of the invention. The contents that are described in this application would be readily apparent to one of ordinary skilled in the art, and thus will not be further described in more detail. Disclosures about techniques or methods related to the present invention can be found in [Rabbit monoclonal antibodies: generating a fusion partner to produce rabbit-rabbit hybridomas. (Proc Natl Acad Sci USA. 1995 92(20):9348-52.)], [Generation of rabbit monoclonal antibodies (Methods Mol Biol., 2014; 1131:71-9)], and [Generation of rabbit monoclonal antibodies (Methods Mol Biol., 2014; 1131:71-9)], wherein in vitro and in vivo methods of preparing hybridoma and obtaining antibodies are described in detail.

In the present invention, the term "antibody" may refer to a molecule that specifically binds to an antigen, and cover dimeric, trimeric, multimeric, recombinant, processed, and camelized antibodies. In addition, the antibody may be in a complete form as well as in a form of a functional fragment of an antibody molecule. As used herein, the term "monoclonal antibody" may refer to antibody molecules of single molecular composition obtained from a substantially identical population of antibodies, and such monoclonal antibodies exhibit a single binding specificity and affinity to a specific epitope. The term "hybridoma cell line" may refer to a hybrid cell line obtained by fusing a tumor cell and a normal cell having an intended function, thereby possessing both of proliferation ability originated from tumor cell and a function of the living cell, and being useful in preparation of monoclonal antibodies and the like.

The term "composition" in the present invention can be used as a composition for preventing and treating a cancer not only in human but also in cattle, horses, sheep, pigs, goats, camels, antelopes, and the like, who can potentially suffer from a cancer.

The term "prevention" used in the present invention may mean all actions to suppress or delay outbreak of a cancer by administering the antibody of the present invention, and the term "treatment" may mean all actions to improve or beneficially change a cancer by administering the antibody of the present invention.

When used as a therapeutic antibody, the antibody can be coupled (for example, covalently bonded) to an existing therapeutic agent directly or indirectly through a linker, and then administered into a body in the form of an antibody-therapeutic agent conjugate, to be used for preventing or treating a cancer. The therapeutic agents may include chemotherapeutic agents, immunotherapeutic agents, cytokines, chemokines, antiviral agents, biological agents, enzyme inhibitors, and the like.

The term "composition comprising an antibody" in the present invention may comprise a pharmaceutically acceptable carrier, and may be formulated for human or veterinary use. The pharmaceutical composition for oral administration may be formulated in individual units, for example, in a form of capsule or tablet; powder or granule; syrup or suspension (in aqueous or non-aqueous liquid; edible foam or whip; or emulsion). The pharmaceutical composition for parenteral administration may include aqueous and non-aqueous sterile injection solution which may comprise an antioxidant, a buffer, a bacteriostat, and a solute (which are substantially isotonic with recipient's blood); and aqueous and non-aqueous sterile suspensions which may comprise a suspending agent and a thickening agent. The excipients that may be comprised in the injection solution may include, for example, water, alcohols, polyols, glycerin and vegetable oils. The composition may be packaged in a unit (single)-dose (one-time) or multi-dose (several-dose) container, such as a sealed ampoule, and may be stored under freeze-drying condition requiring addition of a sterile liquid carrier, e.g., injection water, shortly before use. An Instant injection solution and suspension may be prepared from sterile powders, granules, and tablets.

As used in the present invention, the term "kit" may cover not only the antibody of the present invention but also a tool, a reagent, and the like, which can be conventionally used in immunological analysis. Such tool/reagent may include, but not be limited to, a suitable carrier, a labeling substance capable of generating a detectable signal, a solubilizer, a detergent, a buffer, a stabilizer, and the like. When the labeling substance is an enzyme, it may comprise a substrate capable of measuring enzyme activity and a reaction stopping agent.

As used in the present invention, the term "detection of acetylation degree of BubR1 protein" means qualitative or quantitative measurement of signal intensity of a detection label bound to an antigen-antibody conjugate to determine the presence and amount of acetylated BubR1. Such tool/reagent may include, but not be limited to, a suitable carrier, a labeling substance capable of generating a detectable signal, a solubilizer, a detergent, a buffer, a stabilizer, and the like. When the labeling substance is an enzyme, it may comprise a substrate capable of measuring enzyme activity and a reaction stopping agent.

The formation of an antigen-antibody conjugate can be detected by Immunohistochemical staining, Radioimmunoassay (RIA), Enzyme-Linked Immunosorent Assay, Western Blotting, Immunoprecipitation Assay, Immunodiffusion assay, Complement Fixation Assay, FACS, protein chip, and the like, but not be limited thereto.

The label that enable qualitative or quantitative measurement of the formation of an antigen-antibody conjugate may include, but not be limited to, an enzyme, a fluorescent material, a ligand, a luminescent material, a microparticle, a redox molecule, and a radioisotope. The enzyme that can be used as detection labels may include, but not be limited to, β-glucuronidase, β-D-glucosidase, β-D-galactosidase, urease, peroxidase, alkaline phosphatase, acetylcholinesterase, glucose oxidase, hexokinase, GDPase, RNase, glucose oxidase, luciferase, phosphofructokinase, phosphoenolpyruvate carboxylase, aspartate aminotransferase, phosphoenolpyruvate decarboxylase, β-lactamase, and the like. The fluorescent material may include fluorescein, isothiocyanate, rhodamine, phycoerythrin, phycocyanin, allophycocyanin, o-phthalate, fluorescamine, and the like. The ligand may include, but not be limited to, a biotin derivative. The luminescent material may include, but not be limited to, acridinium ester, luciferin, luciferase, and the like.

The microparticle may include, but not be limited to, colloidal gold, colored latex, and the like. The redox molecule may include, but not be limited to, ferrocene, ruthenium complex, viologen, quinone, Ti ion, Cs ion, diimide, 1,4-benzoquinone, hydroquinone, K4W(CN)8, [Os(bpy)3]2+, [RU(bpy)3]2+, [MO(CN)8]4-, and the like. The radioisotope may include, but not be limited to, 3H, 14C, 32P, 35S, 36Cl, 51Cr, 57Co, 58Co, 59Fe, 90Y, 125I, 131I, 186Re, and the like.

The term "cross-reactivity" used in the present invention may refer to a phenomenon in which there is a plurality of epitopes in one antigen and an antibody specific to one epitope can also bind to other similar epitope. The term "labeling substance" is a substance to detect a target material or phenomenon, and may include, but not be limited to, a fluorescent substance, a radioactive isotope, a ferritin, an enzyme, and the like. The labeling substance can be detected by fluorescence microscopy, radioautography, optical microscope, enzyme reaction, and the like, but not be limited thereto.

Hereinafter, the present invention will be described in more detail with reference to examples.

Example 1 Determination of a Target Peptide Antigen of the Present Invention and Production of Polyclonal Hybridoma Cells An anti-mouse acetylated BubR1 antibody of the present invention was prepared using the information and sequences in Table 1 below. For efficient production of the antibody, the left and right sequences were selected so that the lysine (K) residue is located at the middle position, to select a target peptide (SEQ ID NO: 1) for production of the antibody (Table 1).

TABLE 1

| | |
|---|---|
| mouse BubR1 accession number | Q9Z1S0 |
| Amino acid sequence around the 243$^{rd}$ residue, Lysine(K), of mouse BubR1 | PSIRVGGALKAPGQSR |
| Target peptide (SEQ ID NO: 1) for antibody production | cGGAL(acK)APGQS |

(C: Cysteine; G: Glycine; A: Alanine; L: Leucine; K: Lysine; A: Alanine; P: Proline; G: Glycine; Q: Glutamine; S: Serine; K: Acetylation site)

The target peptide (SEQ ID NO: 1) for antibody production was injected into rabbits, to generate cells producing antibodies against the antigen. Antibody-producing cells (lymphocytes, B cells) obtained from the rabbit spleen were fused with myeloma cells (240E-W2, Abcam®). The fused cells subjected to ELISA, to obtain polyclonal hybridomas in immuneactive multiple cell types or multiclones.

Example 2 Preparation of GST-Tagged Mouse BubR1 (Amino Acids 1-514) Recombinant Protein of the Present Invention and Selection of BubR1-Specific Polyclonal Hybridoma mAbBubR1-SNU-20 Cell the GST-tagged mouse BubR1 (amino acids 1-514) recombinant protein was prepared for selecting polyclonal hybridoma cells specifically recognizing acetylated mouse BubR1 only, by in vitro acetylation experiments of the polyclonal hybridoma cells obtained in Example 1.

The GST-tagged mouse BubR1 (amino acids 1-514) recombinant protein was added with Acetyl-CoA and divided into two groups. The two groups were reacted at 30° C. for 1 hour, wherein GST-P/CAF HAT domain was added to one group and excluded from the other group, to prepare one group (AC) wherein the GST-tagged mouse BubR1 (amino acids 1-514) recombinant protein was acetylated, and other group (NAC) wherein he GST-tagged mouse BubR1 (amino acids 1-514) recombinant protein was not acetylated. The polyclonal hybridoma cell culture broth was added to the above two groups at a ratio of 1:3 in a blocking solution containing 5% defatted milk, followed by electrophoresis and western blotting.

As a result of the western blotting, the mAcBubR1-SNU-20 cells among the polyclonal hybridomas obtained in Example 1 was found to have superiority in specifically recognizing BubR1 containing acetylated 243$^{rd}$ residue lysine, thereby being selected as a polyclonal hybridoma (FIG. 2).

The polyclonal hybridoma cells produced according to this example were named as mAcBubR1-SNU-20, and deposited to Korea Cell Line Bank (101, Daehak-ro, Jongno-gu, Seoul, Republic of Korea), which is International Depository Authority under the Budapest Treaty, on 2017 Jan. 19 with accession No. KCLRF-BP-00390.

Example 3 Selection of Monoclonal Hybridoma Cells from BubR1-Specific Polyclonal Hybridoma mAb BubR1-SNU-20 Cells and Purification of Culture Medium Single-line (ot subclon) hybridoma cells were additionally selected from the polyclonal hybridoma mAb BubR1-SNU-20 cells selected in Example 2. The additionally selected monoclonal hybridoma cells were cultured in RPMI 1640 medium containing 10% FBS (fetal bovine serum), 1% penicillin and streptomycin under the condition of 37° C. and 5% $CO_2$. Each monoclonal antibody contained in the culture medium was further subjected to immunoprecipitation using HeLa cell or mouse embryonic fibroblast and western blotting as in Examples 4 and 5, to select monoclonal antibodies specifically recognizing acetylated mouse BubR1.

Example 4 Examination of Specificity of Monoclonal Antibody to Acetylated Mouse BubR1 by Immunoprecipitation Using HeLa Cells and Western Blotting HeLa cells transfected with Myc-tagged mouse BubR1 (FIG. 3) were treated with nocodazole (200 ng/ml), and synchronized, and then, the culture vessel was gently tapped, to separate cells in metaphase (mitotic shake off). The metaphase cells were collected, and the cell extracts obtained therefrom were subjected to immunoprecipitation with an anti-9E10 antibody, and then, western blotting using the anti-mouse acetylated BubR1 monoclonal antibody of Example 3 in the ratio of 1:5, to screen mAcBubR1-SNU-20-4, mAcBubR1-SNU-20-7, and mAcBubR1-SNU-20-9 as monoclonal antibodies specifically binding thereto (FIG. 4).

The monoclonal hybridoma cells produced according to this example were named as mAcBubR1-SNU-20-4, mAcBubR1-SNU-20-7, and mAcBubR1-SNU-20-9, respectively, and deposited to Korea Cell Line Bank (101, Daehak-ro, Jongno-gu, Seoul, Republic of Korea), which is International Depository Authority under the Budapest Treaty, on 2017.01.19 with accession Nos. KCLRF-BP-00391, KCLRF-BP-00392, and KCLRF-BP-00393, respectively.

Example 5 Examination of Specificity of Monoclonal Antibody to Acetylated Mouse BubR1 by Immunoprecipitation Using Mouse Embryonic Fibroblast and Western Blotting To identify antibodies recognizing endogenous mouse acetylated BubR1, mouse embryonic fibroblasts were treated with nocodazole (400 ng/ml) and then metaphase cells were separated therefrom (mitotic shake off). The separated cells were collected, and subjected to immunoprecipitation using anti-BubR1 antibody for cell extract from the cells, and western blotting using the anti-mouse acetylated BubR1 monoclonal antibodies of Example 4 in the ration of 1:5, to screen mAcBubR1-SNU-20-7 as a monoclonal antibody specifically binding thereto (FIG. 5).

INDUSTRIAL AVAILABILITY

As described above, the present invention provides a monoclonal antibody against rabbit-immunized acetylated mouse BubR1, which has superior specificity and reactivity compared to a mouse monoclonal antibody, and a method for producing the monoclonal antibody. The monoclonal antibody can be used in measuring cell division checkpoint activity using acetylation degree of BubR1 as a scale, detecting a disease associated with abnormal cell division, diagnosing a cancer, and screening an anticancer agent, or regulating cell division cycle; thereby being very useful in diagnosing, preventing, and treating cancer.

SEQUENCE LISTING

<110> Seoul National University R&DB Foundation
<120> A Novel Specific Monoclonal Antibody for acetylated mouse BubR1 and preparation method of the same
<130> P5953
<150> KR 10-2016-0006851
<151> 2016-01-20
<160> 1
<170> Kopatentln 2.0
<210> 1
<211> 11
<212> PRT
<213> Artificial Sequence
<220>
<223> 1
<400> 1
Cys Gly Gly Ala Leu Lys Ala Pro Gly Gln Ser
1               5                   10

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: 1
<220> FEATURE:
<221> NAME/KEY: PEPTIDE
<222> LOCATION: (1)..(11)
<223> OTHER INFORMATION: 6th amino acid Lysine is acetylated.
```

```
<400> SEQUENCE: 1

Cys Gly Gly Ala Leu Lys Ala Pro Gly Gln Ser
1               5                   10
```

The invention claimed is:

1. A monoclonal antibody against acetylated mouse BubR1 produced by a hybridoma selected from the group consisting of mAcBubR1-SNU-20-4 (KCLRF-BP-00391), mAcBubR1-SNU-20-7 (KCLRF-BP-00392), and mAcBubR1-SNU-20-9 (KCLRF-BP-00393).

2. The monoclonal antibody of claim 1, which is produced by mAcBubR1-SNU-20-7 (KCLRF-BP-00392).

3. The monoclonal antibody of claim 2, which is specific to endogenous acetylated mouse BubR1.

4. The monoclonal antibody of claim 1, which does not exhibit cross-reactivity to a mouse BubR1 protein having non-acetylated 243rd residue lysine and a mouse BubR1 protein having substitution of the 243rd residue lysine with arginine.

5. A hybridoma selected from the group consisting of mAcBubR1-SNU-20-4 (KCLRF-BP-00391), mAcBubR1-SNU-20-7 (KCLRF-BP-00392), and mAcBubR1-SNU-20-9 (KCLRF-BP-00393), which produces a monoclonal antibody against acetylated mouse BubR1.

6. A method of detecting acetylation degree of BubR1 protein, comprising determining the acetylation degree of the BubR1 protein using the monoclonal antibody of claim 1.

7. The method of claim 6, wherein the monoclonal antibody is produced by mAcBubR1-SNU-20-7 (KCLRF-BP-00392).

8. The method of claim 7, wherein the acetylation degree is that of endogenous acetylated mouse BubR1.

* * * * *